(12) United States Patent
Longsworth et al.

(10) Patent No.: US 10,704,809 B2
(45) Date of Patent: Jul. 7, 2020

(54) SYSTEM FOR WARMING-UP AND COOLING-DOWN A SUPERCONDUCTING MAGNET

(71) Applicant: SUMITOMO (SHI) CRYOGENICS OF AMERICA, INC., Allentown, PA (US)

(72) Inventors: Ralph C. Longsworth, Allentown, PA (US); Santhosh Kumar Gandla, Allentown, PA (US)

(73) Assignee: SUMITOMO (SHI) CRYOGENICS OF AMERICA, INC., Allentown, PA (US)

( * ) Notice: Subject to any disclaimer, the term of this patent is extended or adjusted under 35 U.S.C. 154(b) by 0 days.

(21) Appl. No.: 16/467,599

(22) PCT Filed: Dec. 20, 2016

(86) PCT No.: PCT/US2016/067734
§ 371 (c)(1),
(2) Date: Jun. 7, 2019

(87) PCT Pub. No.: WO2018/118019
PCT Pub. Date: Jun. 28, 2018

(65) Prior Publication Data
US 2019/0316813 A1 Oct. 17, 2019

(51) Int. Cl.
*F25B 9/14* (2006.01)
*F17C 3/08* (2006.01)
*A61B 5/055* (2006.01)

(52) U.S. Cl.
CPC ............... *F25B 9/14* (2013.01); *F17C 3/085* (2013.01); *A61B 5/055* (2013.01)

(58) Field of Classification Search
CPC ..... F25B 9/14; F25B 2309/1425; F17C 3/085
See application file for complete search history.

(56) References Cited

U.S. PATENT DOCUMENTS 4,279,127 A   7/1981   Longsworth
5,551,488 A   9/1996   Gram
(Continued)

FOREIGN PATENT DOCUMENTS

CN   104154676 A   11/2014
EP     2729705 A1    5/2014
(Continued)

OTHER PUBLICATIONS

International Search Report and Written Opinion dated Aug. 16, 2017, from International Application No. PCT/US2016/067734, 10 sheets.
(Continued)

*Primary Examiner* — Brian M King
(74) *Attorney, Agent, or Firm* — Katten Muchin Rosenman LLP

(57) ABSTRACT

A cryogenic refrigerator system with heaters is constructed in modular form to serve as a portable servicing system to warm up and then cool down a target object by circulating a gaseous cryogen through a target object cryostat without moving the target object or breaking its vacuum. The main module is a refrigerator cryostat containing a fan that circulates gas through one or more heat exchangers which can warm or cool the gas by heaters and by one or more GM or Brayton cycle expanders. Additional components including one or more compressors, a gas charge and vent assembly, a control system, gas lines, power lines, and vacuum jacketed transfer lines can be assembled in the main module or additional modules. An example is a system that can be wheeled through a hospital to service a MRI cryostat.

8 Claims, 2 Drawing Sheets

(56) References Cited

U.S. PATENT DOCUMENTS

| | | | |
|---|---|---|---|
| 6,256,997 B1 | 7/2001 | Longsworth | |
| 6,347,522 B1 | 2/2002 | Maguire et al. | |
| 6,940,009 B2 | 9/2005 | Damian Alvarez | |
| 8,448,461 B2 * | 5/2013 | Longsworth | F25B 9/14 62/401 |
| 2005/0086974 A1 * | 4/2005 | Steinbach | F25B 9/14 62/437 |
| 2007/0214821 A1 * | 9/2007 | Astra | F25D 3/10 62/259.2 |
| 2012/0047913 A1 | 3/2012 | Mizuno | |
| 2013/0067952 A1 | 3/2013 | Rl et al. | |
| 2015/0354865 A1 | 12/2015 | Longsworth | |

FOREIGN PATENT DOCUMENTS

| | | |
|---|---|---|
| GB | 2433581 A | 6/2007 |
| JP | 5579259 B2 | 8/2014 |
| KR | 1020120047913 A | 5/2012 |
| KR | 1020130090565 A | 8/2013 |
| WO | 2013/006299 A1 | 1/2013 |

OTHER PUBLICATIONS

Korean Office Action dated Nov. 18, 2019, for the Corresponding Korean Patent Application No. 10-2019-7021354.

Extended European Search Report dated Nov. 25, 2019, for the Corresponding European Patent Application No. 16924333.4.

Japanese Office Action dated Dec. 17, 2019, for the Corresponding Japanese Patent Application No. 2019-533647.

Korean Notice of Allowance dated Apr. 21, 2020, for the Corresponding Korean Patent Application No. 10-2019-7021354.

* cited by examiner

SYSTEM FOR WARMING-UP AND COOLING-DOWN A SUPERCONDUCTING MAGNET

BACKGROUND OF THE INVENTION

1. Field of the Invention

This invention relates to warming a target object that is cooled by a cryogenic refrigeration system i.e., a cryogen in a cryostat, from cryogenic temperature to ambient temperatures so that it can be serviced then cooled to cryogenic temperatures without moving the cryostat and without breaking vacuum.

2. Background Information

Cryogenic refrigeration systems may cool superconducting magnets, for example, in magnetic resonance imaging (MRI) cryostats, to cryogenic temperatures. The superconducting magnet typically operates in a bath of liquid helium and is cooled by the cryogenic refrigeration system. The superconducting magnet occasionally needs to be warmed to room temperature to be serviced and, after servicing, then be cooled down again. Ideally, this is accomplished without the magnets being moved and without breaking vacuum.

Herein, cryogenic temperatures are defined as less than 100 K or −173° C. and ambient temperatures are 273 K or 0° C. or greater. Devices, systems, or objects being cooled by one or more cryogenic refrigeration systems are referred to as one or more "target objects" or one or more "cold objects." The target object or cold object is typically disposed directly or indirectly in a cryogen, such as helium. The target object or cold object is cooled by the cryogen.

Additionally, there are many target objects operating at cryogenic temperatures, from small infrared detectors that are cooled by direct contact to a cold end of a small Stirling or GM type refrigerator (i.e., cryogenic refrigeration systems, to large assemblies of superconducting magnets in accelerators that are cooled by circulating helium that is cooled by large turbo-Brayton type refrigerators. There are many different ways to warm up a target object including simply turning off the refrigerator, turning off the refrigerator and warming the target object with a heater, passing a current through the target object, circulating a warm gas, and breaking the vacuum.

U.S. Pat. No. 8,448,461 by Longsworth describes an engine operating on the Brayton cycle that is designed for fast cool down of a MRI magnet to less than 40 K. A refrigerator that incorporates this Brayton cycle engine consists of a compressor that supplies gas at a discharge pressure of about 2 MPa to a counterflow heat exchanger, from which gas is admitted to an expansion space at the cold end of the engine through an inlet valve, expands the gas adiabatically to about 0.8 MPa, exhausts the expanded gas (which is colder) through in outlet valve, circulates the cold gas through vacuum jacketed transfer lines to the magnet cryostat, then returns the gas through the counterflow heat exchanger to the compressor.

An MRI cryostat that can be cooled by helium at pressures as high as 1 MPa has been developed recently. Most of the MRI magnets built to date though have been designed to operate with the helium at atmospheric pressure. 0.1 MPa, and to withstand a maximum pressure of about 0.3 MPa. A Brayton cycle engine with an exhaust pressure of 0.8 MPa can be used to cool a gas at the lower pressures by transferring the heat from the gas that is circulated through the magnet cryostat at the low pressure to the gas in the refrigerator, which is at a higher pressure, in a counterflow heat exchanger. While it is possible to put this heat exchanger at the magnet cryostat to cool down the magnet, as described in US patent application 2015/0354865 by Longsworth, it is preferred to put this heat exchanger in the refrigerator cryostat where it can be more easily integrated with additional components that are required to service the magnet.

The principles that enable the expander of the '461 patent to cool down fast are the 1) the ability to run it a speed above cryogenic temperatures that does not allow gas to by-pass from high to low pressure and 2) reducing the speed as it cools down while gas is added from a gas storage tank in order to maintain constant high and low (supply and return) pressures. These same principals apply to a GM cycle refrigerator except that the cold volume in a GM refrigerator is small enough that a separate gas storage tank is usually not needed. This is because gas volumes in the compressor, oil separator, and adsorber are sufficient to keep the pressure reductions small enough during cool down to cause only a small reduction in cooling capacity.

A GM cycle refrigerator comprises a compressor that supplies gas through gas lines at a discharge pressure of about 2 MPa to an expander that has inlet and outlet valves at the warm end of a cylinder containing a reciprocating piston/regenerator assembly, the inlet valve supplying discharge pressure gas through the regenerator to a cold end while the piston is at the cold end and as it moves to the warm end, then returns gas through the outlet valve to the compressor at a return pressure of about 0.8 MPa while the piston is at the warm end and as it moves to the cold end. An example of a preferred configuration of a GM cycle expander is described in U.S. Pat. No. 6,256,997.

U.S. Pat. No. 6,347,522 by Maguire et al. describes a cooling system for HTS machines that incorporates multiple GM expanders in a refrigerator cryostat along with a means to circulate gas that is cooled by the expanders through supply and return transfer lines connected to a cryostat containing a superconducting Rotor. The GM expanders are connected to a bank of compressors that supply gas to the expanders through manifolded gas lines. The means to circulate gas include one or two fans in the refrigerator cryostat during cool down and by rotation of a superconducting rotor after cool down.

Single stage GM and Brayton cycle refrigerators that operate with helium as a refrigerant can provide refrigeration at temperatures as low as about 12 K. A simpler cooling system that uses liquid nitrogen can be used but it can only cool a target object to about 80 K. Such a system is described in U.S. Pat. No. 6,940,009 by Kudaravalli. This system comprises a circulator at room temperature, a counter-flow heat exchanger that precools the supply gas with the return gas, a heat exchanger cooled by liquid nitrogen, and lines that enable the cold gas to flow through the magnet.

Neither the '522 patent or the '009 patent state the pressure of the circulating gas but it is implied to be slightly above atmospheric pressure. UK patent G 2 433 581 by Atkins et al describes a general system that circulates gas that is cooled by a cold surface through lines that connect to a cryostat at a pressure below 200 KPa above atmospheric pressure.

SUMMARY OF THE INVENTION

In accordance with one or more embodiments of the present invention, the servicing system has been designed to warm up and cool down a superconducting magnet in a MRI cryostat which operates in a bath of liquid helium, in what is referred to here as a system cryostat, it can also be used to warm up and cool down other systems such as superconducting motors, generators, transformers, fault current limiters, etc. that are cooled by other cryogenic gases or liquids such as neon and nitrogen. In general it can best be used to warm and cool systems that operate below 100 K.

This invention is a portable servicing system to warm up then cool down a target object that can be warmed and cooled by circulating a gaseous cryogen through a cryostat without moving the cryostat or breaking its vacuum. Typically, the cryostat is maintained at a cryogenic temperature by a separate refrigerator. The servicing system comprises several modules that can be easily moved to the site of a target object cryostat that needs to be serviced.

The main module is a refrigerator cryostat comprising a fan that circulates gas in a circulation circuit through one or more heat exchangers with means to warm the gas and one or more heat exchangers cooled by one or more GM or Brayton cycle expanders that cools the gas, the circulation circuit including vacuum jacketed lines that connect to a target object cryostat. One or more compressor modules are connected to the one or more expanders through high and low pressure gas lines, preferably the lines from one compressor connected to one expander in contrast to the compressors and expanders being connected to supply and return manifolds.

The portable servicing system includes a controller connected to essential sensors, charge vent and safety valves, and a vacuum pump, all of which can be part of a separate module or preferably part of the refrigerator module. The control system controls the warm up and cool down of the target object by controlling fan speed, heater power, and expander speed such that warm up time and cool down time are minimized. Gas is circulated at a pressure below 200 kPa so that it can be used on any target object cryostat that has been designed to operate at a higher pressure.

The present invention is designed as a service system for intermediate size cryogenic systems that can be warmed and cooled by circulating gas and that can be cooled to an acceptable temperature by the cooling capacity of the present invention which is limited by the requirement that the modules of the system can be moved through a 76 cm wide door by one or two people. The service system has two vacuum jacketed transfer lines that need to be inserted in two bayonet ports on the cryostat being serviced. One or both of these two bayonet ports can either be designed into the cryostat or designed into a servicing cryostat that replaces an existing cover on the cryostat. It is preferred that one port delivers gas to or returns gas from the bottom of the cryostat and that the other supplies gas to or returns gas from the top of the cryostat. In order for the transfer lines to fit into either port, in order to reverse the direction of flow through the system cryostat, the bayonets on the two transfer lines have to be identical and the two receptacles on the system cryostat have to be compatible with the transfer line bayonets.

The refrigerators of the present invention are designed to cool the system down, not to keep it cold. For example, the system that has been built is designed to cool a superconducting MRI magnet to less than 40 K in less than a week. At that point the system is removed and the balance of the cooling to 4 K is done with liquid helium. If a particular magnet for example requires 2,000 L of liquid helium to cool it from 295 K to 4 K, it would require about 780 L if it is precooled to 80 K (by liquid nitrogen), or it would require about 170 L if cooled to 40 K (by a refrigerator), or it would only require about 100 L if cooled to 30 K. Typically the refrigerator that keeps the magnet cold is turned on at some point in the cool down and used to continue the cool down after the service system has been removed.

DESCRIPTIONS OF THE PREFERRED EMBODIMENTS

Figure 1:
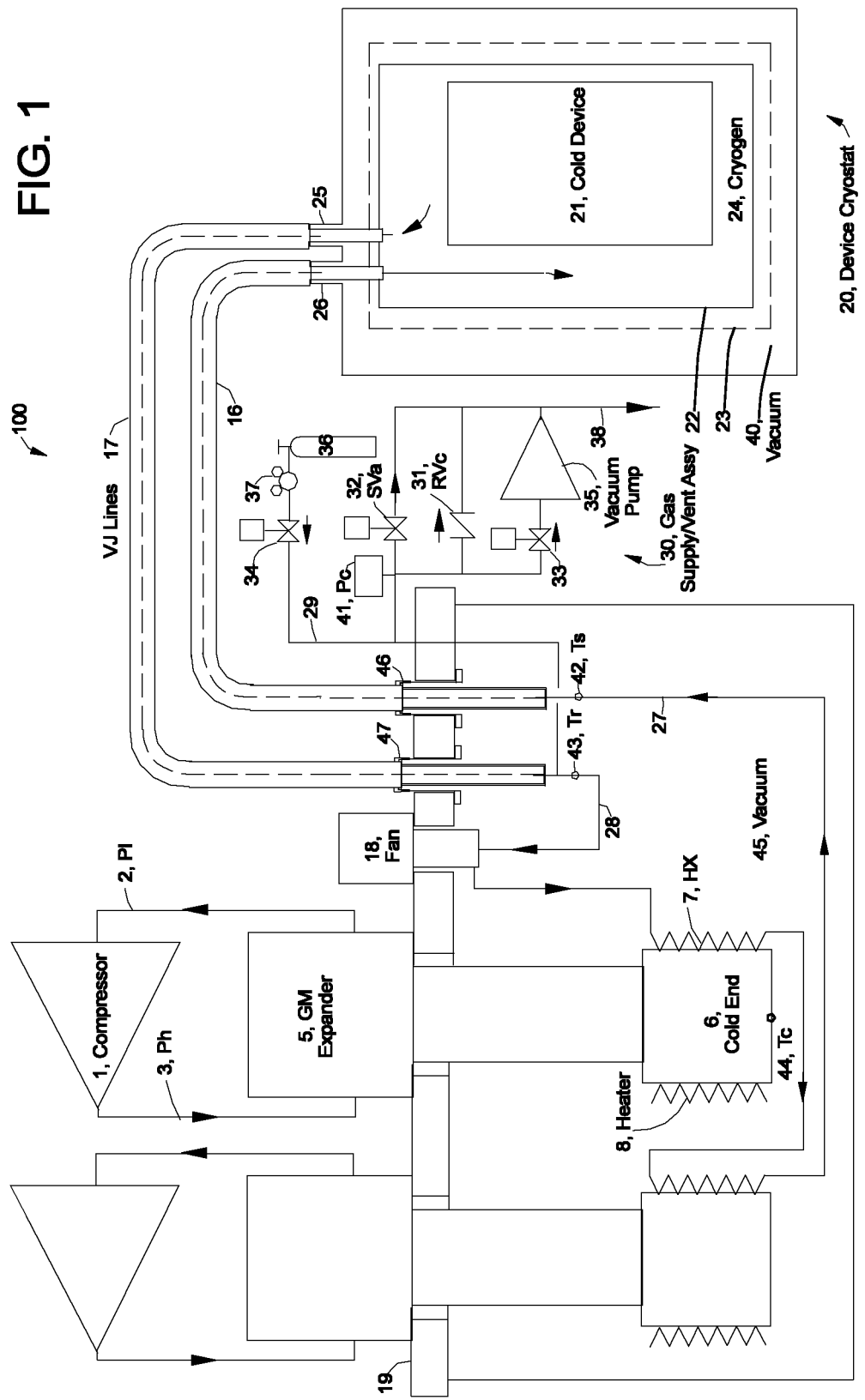
FIG. 1 is a schematic of system 100 which has one or more compressors connected to one or more GM type expanders in a refrigerator cryostat which also contains a circulator that circulates gas that is heated or cooled through vacuum jacketed transfer lines to a target object cryostat.
Figure 2:
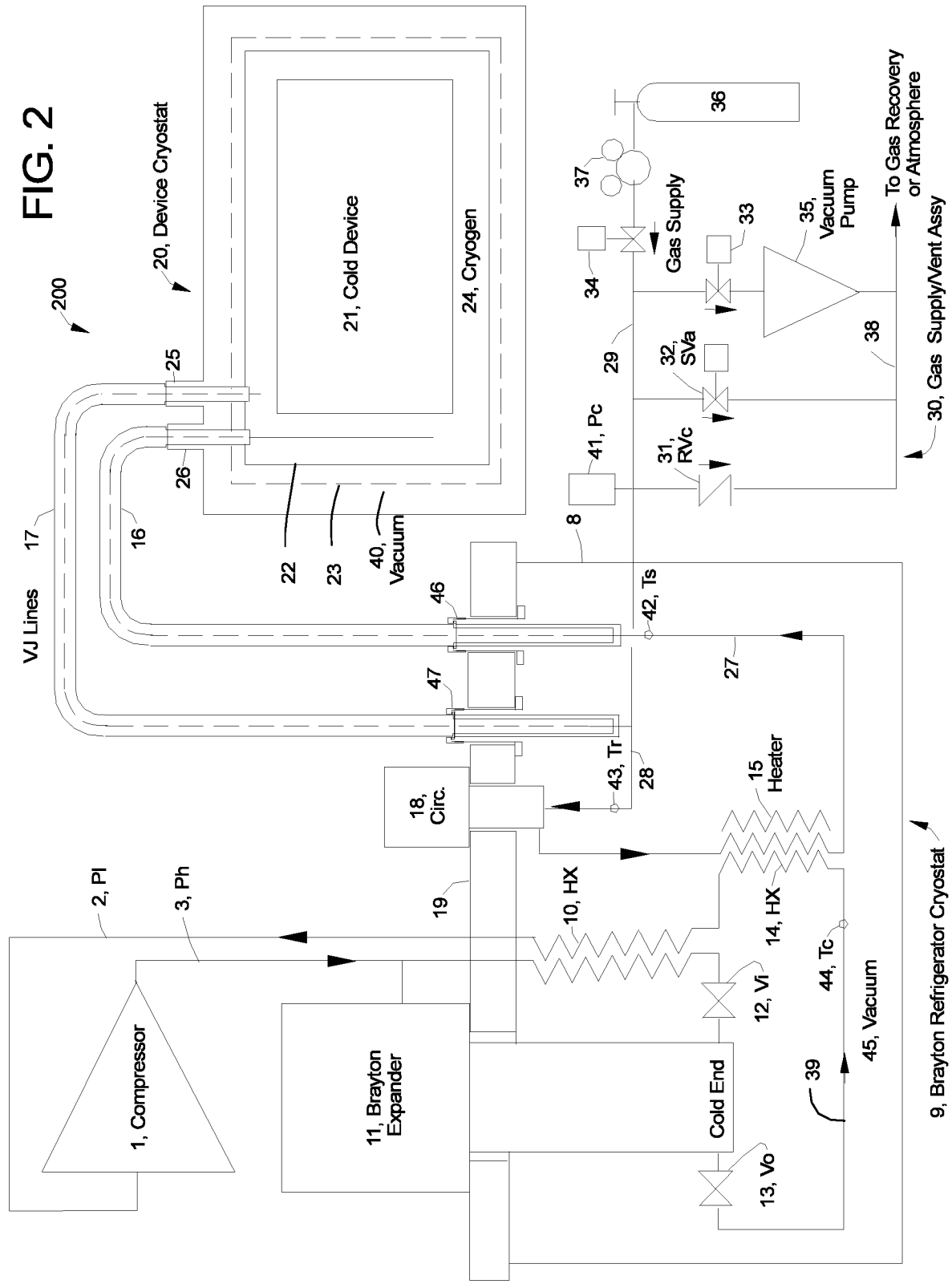
FIG. 2 is a schematic of system 200 which has one or more compressors connected to one or more Brayton type expanders in a refrigerator cryostat which also contains a circulator that circulates gas that is heated or cooled through vacuum jacketed transfer lines to a target object cryostat.

The components that are shown in FIGS. 1 and 2 use the same number and the same diagrammatic representation to identify equivalent parts. Since cold gas is denser than warm gas most of the components are shown with the cold end down. Components that are at cryogenic temperatures, <100 K in the present case, are thermally insulated from the surrounding ambient by vacuum, <0.1 Pa, within a housing, the assembly being referred to as a cryostat.

FIG. 1 is a schematic of system 100 showing one GM refrigerator with identifying numbers and a second without numbers that also represents additional refrigerators. A typical GM refrigerator consists of a compressor, 1, a low pressure (return) line, 2, at a pressure of about 0.8 MPa, a high pressure (supply) line, 2, at a pressure of about 2 MPa, and an expander 5. The present servicing system that has been built and tested uses four single stage GM expanders which have been designed to have a minimum temperature of about 12 K. For the present application it is more important for the refrigerator to have a high capacity close to room temperature because the specific heat of materials is higher at room temperature than at cryogenic temperatures. For example a MRI magnet that has 300 MJ of heat to be removed between 300 K and 4 K only has about 55 MJ to be removed between 100 K and 4 K.

The expanders in the present system are designed to operate at a higher speed near room temperature than when they are below 100 K. In a GM refrigerator cooling is available at cold end 6 which is typically a copper sleeve. It is preferred to build into cold end 6 heat exchanger 7 which consists of slots or holes through which gas that is circulated by fan 18 can transfer heat from target object cryostat 20 to cold end 6. To warm target object 21 in target object cryostat 20 it is preferred to have electric heater 8 wrapped around the outside of the copper sleeve and use circulating fan 18 to circulate heated gas through supply gas line 27, supply vacuum jacketed transfer line 16, through target object cryostat 20, return vacuum jacketed transfer line 17, and through gas return line 28 to fan 18. This circuit is referred to in this document as either the fan circuit, or the circulation circuit, both of which may or may not include target object cryostat 20. Transfer lines 16 and 17 are removable from bayonet receptacles 46 and 47 in refrigerator cryostat 4, and from ports 25 and 26 in target object cryostat 20. Heater 8 can be located elsewhere along line 27.

If there is only one expander 5 then gas is circulated through only one gas heat exchanger 7. For two expanders it is preferred to have the circulating gas flow through heat exchangers 7 in series. If they were connected in parallel and one refrigerator is off then the circulating flow is split and only half is cooled. This is less efficient than having all of the circulating gas cooled to the same temperature for the case when they are connected in series and only one refrigerator is operating. This same logic applies to adding more refrigerators. It is preferred that they be added in pairs.

System cryostat 20 is shown as a generic cryostat that keeps target object 21 cold while it is operating. Target object 21 is shown inside container 22 and surrounded by cryogen 24, e.g. helium, neon, or nitrogen. The cold components target object cryostat 20 are thermally insulated from room temperature by vacuum 40, cold shield 23, and radiation shielding which is not shown. Ports 25 and 26 in target object cryostat 20, into which transfer lines 16 and 17 are inserted, are shown as terminating near the top and bottom of the cryostat. Since gas stratifies in container 22, it is desirable when cooling target object 21 to have cold gas flow to the bottom of the cryostat and warmer gas be removed from the top, as indicated by the arrows, and to reverse the flow when warming the magnet so that warm gas flows into the top of the cryostat and cold gas flows out the bottom. Fan 18 circulates gas in only one direction and thus the bayonets must be identical so that transfer lines 16 and 17 can be switched in ports 25 and 26 when changing from warming the target object to cooling it.

FIG. 2 is a schematic of system 200 showing one Brayton cycle refrigerator. Additional Brayton cycle refrigerators can be added with the expander (engine) for each mounted in Brayton refrigerator cryostat 9. A GM expander has valves internal to the warm end of the expander that cycle gas through a regenerator heat exchanger to the cold end. In a Brayton expander these functions are external to cylinder that contains a reciprocating piston. Counter-flow heat exchanger 10 serves the same function as the GM regenerator and inlet valve 12 and outlet valve 13, which are at the cold end, serve the same function as the warm valves in the GM expander. A Brayton expander has the advantage over a GM expander in circulating cold gas through a line, such as line 39, to a remote load. In this case gas line 39 flows through counterflow heat exchanger 14 where it cools gas being circulated by fan 18 to cool down target object 21 in target object cryostat 20. Heat exchanger 14 is typically a parallel plate type heat exchanger that brings fluids flowing between thin sheets of metal into thermal contact. If an additional Brayton refrigerator were to be added, the gas in that refrigerator would be kept separate from any other refrigerator. Cold gas flowing through a second cold gas line 39 would flow through separate channels in heat exchanger 14. To warm up target object 21, a heater 15 is put in thermal contact with the gas in supply line 27. This can be done by wrapping an electrical heater around a parallel plate heat exchanger if it is used for heat exchanger 14 or by adding a separate heat exchanger in line 27. Compressor(s) 1 and gas lines 2 and 3 can be the same as those shown in FIG. 1. The cold components in GM refrigerator cryostat 4 and Brayton refrigerator cryostat 9 are thermally insulated from room temperature by vacuum 45 and radiation shielding which is not shown. Other components including cover plate 19, bayonet receptacles 46 and 47, and temperature sensors 42 and 43 are the same for both refrigerator cryostats.

Systems 100 and 200 have the same gas supply/vent assemblies that connect through line 29 to return line 28 inside the refrigerator cryostats. Gas is added to the gas circulation lines during cool down, or while purging the lines, from gas cylinder 36, with the pressure regulated by regulator 37, by opening valve 34. Gas is removed from the gas circulation lines during warm up by opening valve 32 which vents gas through line 38 to atmosphere or a gas recovery system. In the event of an overpressure gas vents through pressure relief valve 31 to vent line 38. Typically gas circulates through the circulation lines at a pressure of about 100 kPa above atmospheric pressure and relief valve 31 opens at about 200 kPa. In the event that transfer lines 16 and 17 have been removed after the target object has been warmed up vacuum pump 35 is used to evacuate the gas circulation lines and container 22 before cool down is started. Line 29 connects to valve 33 which is in the inlet line to vacuum pump 35 which in turn vents to line 38. Valves 32, 33, and 34 are all solenoid type valves that can be opened and closed by the control system that is part of the warm up/cool down service servicing system but is not shown. Pressure sensor 41 measures the pressure in the gas circulation lines and sensors 42 and 43 measure the key temperatures that are needed to control the system.

The warm up/cool down service servicing system is comprised of modules that can be moved to the site of a cryogenic target object by being rolled on mobile carts or carried along level floors and through doors by one or two service people. This criteria is defined by a maximum weight of a module of 400 kg and a maximum width to fit through a door of 76 cm. The modules on wheels are the refrigerator cryostat, 4 and 9, which preferably includes the gas supply/vent assembly 30, each compressor, 1, and one with the controller and electrical and refrigerator gas lines 2 and 3. The vacuum jacketed transfer lines, 16 and 17, which tend to be bulky, can be carried.

After bringing the components of the service servicing system to the site, i.e., the servicing system is mobile, along with a cylinder of gas, 36, gas lines 2 and 3, which have self-sealing couplings, are connected to the compressors and expanders along with the electrical lines. Transfer lines 16 and 17 are inserted into bayonets 46 and 47 respectively and caps put on the far end. When activated, the control system starts the vacuum pump 35 and opens valve 33 to evacuate the gas circulation lines until a preset pressure as measured by pressure sensor 41 is reached. Valve 33 is then closed and valve 34 opened to add gas from gas cylinder 36. Valve 34 is then closed and the process is repeated several times in order to leave only the desired cryogen in the lines. The pressure in the cryostat being serviced is brought to atmospheric pressure and a service servicing system that has ports 25 and 26 is then installed in the cryostat. The cap is then removed from supply transfer line 16 as a purge is maintained while inserting it into port 25. Then the cap is removed from return transfer line 17 as a purge is maintained while inserting it into port 26.

Care is needed when starting the target object warm up because there may be liquid cryogen in container 22 that can cause a rapid rise in pressure if heated rapidly. Cryogenic cryostats have a safety burst disc that is expensive; so, a sudden surge of pressure should be avoided. Warm up is started by opening valve 32 that vents gas to atmosphere or a gas recovery system near atmospheric pressure. Circulator fan 18 is then started and the speed increased slowly until the pressure at sensor 41 is at about 100 kPa, a pressure that will not cause gas to vent through relief valve 31.

The speed of fan 18 is increased by the controller as piping in the gas circulation line cools down and the pressure decreases. When the fan has reached its maximum speed and the pressure is less than about 100 kPa the controller turns on heater 8 or 15 and controls the power input such that a pressure of about 100 kPa is maintained. The controller monitors the temperature of the gas at sensor 42 going to target object cryostat 20 and reduces the heat input so that target object 21 is not heated above a preset temperature. When heater 8 or 15 is turned off there will be little difference between temperature sensors 42 and 43, which will also be the temperature of target object 21.

Transfer lines 16 and 17 are preferably removed during service of target object cryostat 20 because they will be inserted in different ports for cool down, line 16 in port 26 and line 17 in port 25. Prior to starting cool down the gas circulating lines and gas container 22 in target object cryostat 20 have to be evacuated and charged with clean cryogen. The same program in the controller that evacuated and charged the gas circulating lines prior to warm up is used to evacuate and charge those same lines plus container 22.

With clean gas in the gas circulating circuit and valve 34 open, to allow gas to feed into the circuit, the refrigerators are started and fan 18 turned on. The controller starts expanders 5 or 11 and fan 18 at max speed and reduces their speeds to minimize cool down time as target object 21 gets colder. During cool down the pressure in the circulating circuit is kept close to the vent pressure so that the density of the gas flowing through the fan is as high as possible in order to maximize the mass flow rate of the circulating gas. In order not to have to vent gas to bring it down to atmospheric pressure when target object 21 reaches minimum temperature valve 34 is closed at a temperature where additional cooling of the gas will bring it to atmospheric pressure.

A servicing system that has been built and tested with GM refrigerators as shown in FIG. 1 is now described. The servicing system has four model CH110LT expanders and four model F70 compressors manufactured by the assignee. Each expander has a capacity of about 400 W at 300 K and a minimum temperature with no load of 12 K. Each of the compressors is mounted on a base with wheels. The four expanders are mounted on cover plate 19 of the refrigerator cryostat and are connected in the fan circuit as two pairs in parallel. Each cold end 6 has channels that form heat exchanger 7 for cooling the circulating helium. 400 W heaters, 15, are wrapped around each of the cold ends.

Also, mounted on the cover plate 19 is a gas circulating fan, Cryozone Nodin 85 mm cryofan. This fan can be operated at speeds from 0 to 18,000 rpm and at max speed has a head of 325 m at 0 flow and a flow of 78 m^3/hr at 0 head. This fan requires a circulation circuit with relatively low pressure drop so that it can circulate about 3 g/s of helium at a pressure of 150 kPa gauge with a fan speed of 18,000 rpm at room temperature. The fan speed is reduced and the flow rate is increased as the system cools down and the gas becomes denser. Vacuum pump 35 is an Edwards nXDS 15i which can pump down a volume of 1,000 L from 100 kPa to 10 kPa in about 50 minutes. Each of the compressors weighs less than 150 kg and is <100 cm wide. The refrigerator cryostat which also has the charge vent assembly (except the gas tank) weighs 375 kg and is 76 cm wide. The vacuum jacketed transfer lines are 5 m long.

In accordance with one or more embodiments of the present invention, a method may be performed using the servicing system. The method may substantially or in part comprise a test that was conducted. A test was run by first cooling a superconducting MRI magnet down then warming it up. A servicing system that had two ports for bayonets was inserted in a port in the magnet cryostat. The procedure described above was then followed, connecting the gas and electrical lines, then the transfer lines, then evacuating and charging the gas circulating circuit including the MRI cryostat. The refrigerator system was then turned on, the helium held at 100 kPa gauge pressure, and the magnet cooled to <30 K in 3.2 days. The MRI cryostat had a RDK 415 expander mounted in it to keep the magnet cold which was then turned on and the temperature brought to 22 K before the transfer lines were removed. About 100 L of liquid helium was then added to bring the magnet to 4.2 K. Some additional liquid helium was added before starting the warm up test. The MRI cryostat had a burst disc that was set at a higher pressure than the relief valve on the warm up/cool down servicing system.

Warm up was accomplished following the procedure described above by first capping off the transfer lines, then evacuating and charging them, and then inserting the transfer lines in the bayonet ports on the MRI cryostat. This test was run with the assumption that some gas might have been adsorbed in the getter that was bonded to the cold container which might outgas and break the insulating vacuum so a turbomolecular vacuum pump was connected to the vacuum pumpout port and operated. Vent valve 32 was opened and fan 18 started at a low speed. The fan speed was increased slowly based on maintaining the circulation circuit at a pressure of about 100 kPa as gas vented through Vent valve 32. When the fan speed reached 18,000 rpm and the pressure started to drop, the power to heaters 8 was slowly increased as temperatures within the MRI cryostat were monitored and the speed controlled to avoid large thermal gradients. Vent valve 32 was closed and gas allowed to vent through relief valve 31 at an increased pressure in order to increase the mass flow rate in the circulating circuit. Maximum power input during warm up was 1,500 W. The MRI magnet warmed to 230 K in 1.2 days at which point the temperature entering the fan, Tr 43, reached 290 K and the heater power was slowly reduced to keep Tr 43 at 290 K over the next 2.4 days while the MRI magnet warmed to 280 K. The warm up/cool down servicing system used in this experiment could have been set to have a maximum return temperature, Tr 43, of 310 K.

The test illustrates the versatility in using this servicing system to warm up and cool down a wide range of cryogenic target objects that operate below 100 K. A servicing system that has multiple refrigerators can be used without bringing all of the compressors to the site. Warm up rates can be controlled by adjusting the fan speed and the heater power. Depending on heat losses in the target object cryostat, minimum temperature after cool down can be as low as 20 K.

What is claimed is:

1. A servicing system for servicing a target object disposed in a target object cryostat, the servicing system comprising:
   one or more expanders and one or more compressors for cooling-down the target object to a cryogenic temperature;
   one or more heaters for warming-up the target object from the cryogenic temperature;
   a fan and a fan circuit, the fan circulating gas through the fan circuit; and
   a refrigerator cryostat housing the one or more expanders and the fan which are surrounded by a vacuum;
   a plurality of heat exchangers for transferring heat from the heater to the gas in the fan circuit during warm-up of the target object and for transferring heat from the target object to the gas in the fan circuit during cool-down of the target object;
   a controller and a plurality of sensors, the plurality of sensors for measuring a temperature and a pressure in the fan circuit, the controller responsive to the plurality of sensors controlling at least a speed of the fan, a speed of the expanders, and a power of the heaters;

a removable supply transfer line for bringing gas from the fan circuit to the target object cryostat;

a removable return transfer line for returning gas from the target object to the fan circuit, the transfer lines being interchangeably connected to the target object cryostat;

a pressure relief valve for relieving excess pressure in the fan circuit; and a vent valve that can be actuated to open to one of atmospheric pressure and a gas recovery system.

2. A system in accordance with claim 1, further comprising a cart for moving the servicing system, the cart and servicing system fitting through a 78 cm wide and 160 cm high doorway.

3. A system in accordance with claim 1, wherein each expander is a GM type expander and each heat exchanger is an integral part of a respective cold end of the expander.

4. A system in accordance with claim 1, wherein each expander is a Brayton type expander and each heat exchanger is separate from a respective cold end of the expander.

5. A system in accordance with claim 1, wherein the heat exchanger for cooling the gas is different from the heat exchanger that warms the gas.

6. A system in accordance with claim 1, wherein the pressure relief valves are set to relieve excess pressure in the fan circuit of less than 200 kPa above atmospheric pressure.

7. A method of servicing a target object disposed in a target object cryostat using a service system, the target object cryostat having a supply port for receiving cold gas during cool down and a return port, the service system comprising:

one or more expanders and one or more compressors for cooling-down the target object to a cryogenic temperature;

one or more heaters for warming-up the target object from the cryogenic temperature;

a fan and a fan circuit, the fan circulating gas through the fan circuit; and a refrigerator cryostat housing the one or more expanders and the fan which are surrounded by a vacuum;

a plurality of heat exchangers for transferring heat from the heater to the gas in the fan circuit during warm-up of the target object and for transferring heat from the target object to the gas in the fan circuit during cool-down of the target object;

a controller and a plurality of sensors, the plurality of sensors for measuring a temperature and a pressure in the fan circuit, the controller responsive to the plurality of sensors controlling at least a speed of the fan, a speed of the expander, and a power of the heaters;

a removable supply transfer line for bringing gas from the fan circuit to the target object cryostat;

a removable return transfer line for returning gas from the target object to the fan circuit, the transfer lines being interchangeably connected to the target object cryostat;

a pressure relief valve for relieving excess pressure in the fan circuit; and a vent valve that can be actuated to open to one of atmospheric pressure and a gas recovery system;

the method comprising the steps of:
(a) inserting proximal ends of the transfer lines in the refrigerator cryostat,
(b) capping distal ends of the transfer lines,
(c) evacuating then filling the fan circuit in the refrigerator cryostat and transfer lines with the cryogen disposed in the target object cryostat,
(d) maintaining a purge with the same cryogen as in step (c) while connecting the return transfer line to a supply port in the target object cryostat,
(e) maintaining a purge with the same cryogen as step (c) while connecting the supply transfer line to a return port in the target object cryostat,
(f) opening the vent valve,
(g) increasing the fan speed then controlling it such that gas does not vent through the relief valve,
(h) controlling fan speed and heater power to warm the target object, and
(i) removing said supply and return transfer lines from said target object cryostat.

8. The method of claim 7, further comprising the steps of servicing the target object cryostat connecting the supply transfer line to a supply port in the target object cryostat, connecting the return transfer line to a return port in the target object cryostat, evacuating then filling the fan circuit in the refrigerator cryostat and the target object cryostat with the same gas as used in the target object cryostat, and operating the expanders and compressors and controlling the fan speed and expander speed while supplying the same gas used to cool down the target object cryostat.

* * * * *